United States Patent [19]

Pfirmann et al.

[11] Patent Number: 5,473,095
[45] Date of Patent: Dec. 5, 1995

[54] PROCESS FOR THE PREPARATION OF CHLORINATED 4,5-DIFLUOROBENZOIC ACIDS, -BENZOIC ACID DERIVATIVES AND -BENZALDEHYDES

[75] Inventors: Ralf Pfirmann, Griesheim; Theodor Papenfuhs, Frankfurt; Georg Weichselbaumer, Kelkheim, all of Germany

[73] Assignee: Hoechst Aktiengesellschaft, Frankfurt, Germany

[21] Appl. No.: 187,622

[22] Filed: Jan. 27, 1994

[30] Foreign Application Priority Data

Jan. 29, 1993 [DE] Germany .......................... 43 02 458.0

[51] Int. Cl.⁶ ...................... C07C 253/30; C07C 51/363; C07C 51/60
[52] U.S. Cl. ............................ 558/425; 562/861; 562/862; 562/863; 562/864; 562/493; 564/183
[58] Field of Search ............................ 558/425; 562/463, 562/861, 862, 863, 864, 493; 564/183

[56] References Cited

U.S. PATENT DOCUMENTS 5,021,605  6/1991  Kobayashi et al. ...................... 558/424
5,187,295  2/1993  Schach ................................. 558/425 X
5,214,187  5/1993  Wolf et al. ............................ 558/425 X

FOREIGN PATENT DOCUMENTS

4123322A1  1/1993  Germany .

OTHER PUBLICATIONS

Patent Abstracts of Japan, vol. 14, No. 356, Aug. 2, 1990.

Primary Examiner—Joseph Paul Brust
Attorney, Agent, or Firm—Connolly and Hutz

[57] ABSTRACT

The present invention relates to a process for the preparation of compounds of the formula

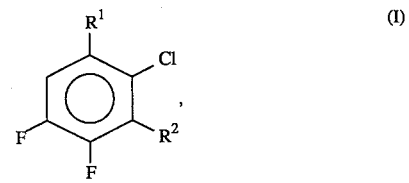

in which $R^1$ is —CN, —COOH, —COOR', R' being an organic radical having 1 to 6 carbon atoms, —CONH$_2$, —COCl or —CHO and $R^2$ is H or Cl, which comprises reacting a compound of the formula

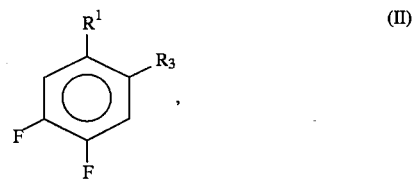

in which $R^1$ is as defined above and $R^3$ is H or Cl, with a chlorinating agent in the presence of a chlorination catalyst at −10° to 200° C.

15 Claims, No Drawings

PROCESS FOR THE PREPARATION OF CHLORINATED 4,5-DIFLUOROBENZOIC ACIDS, -BENZOIC ACID DERIVATIVES AND -BENZALDEHYDES

The present invention relates to a novel and advantageous process for the preparation of 4,5-difluorobenzoic acids, -benzoic acid derivatives and -benzaldehydes chlorinated in the 2-position and optionally in the 3-position. The compounds accessible via the process according to the invention are valuable intermediates for the preparation of highly active antibacterial agents.

2-Chloro-4,5-difluorobenzoic acid is an important intermediate for the synthesis of fluoroquinolonecarboxylic acid drugs. The preparation of these active substances is described in EP-A-0,442,849, EP-A-0,321,191 and EP-A-0,303,291. The conversion of 2,3-dichloro-4,5-difluorobenzoic acid to quinolonecarboxylic acid anti-infective agents can be found for example in German Offenlegungsschrift 3,635,218 and EP-A-0,198,192.

The only synthesis routes known hitherto for the preparation of 2-chloro-4,5-difluorobenzoic acid are unsatisfactory or industrially impracticable. Thus, according to EP-A-0,411,252, 3,4-difluorochlorobenzene can be reacted with chloroacetyl chloride or dichloroacetyl chloride to give the corresponding chlorinated acetophenone derivative, which can be converted to 2-chloro-4,5-difluorobenzoic acid by means of sodium hypochlorite solution (haloform reaction). The use of sodium hypochlorite solution on the one hand represents a significant cost factor and on the other hand results in the production of a considerable quantity of undesirable effluent. Furthermore, the 1,2-difluorobenzene required for the preparation of 3,4-difluorochlorobenzene can only be prepared with great effort by the Schiemann reaction. Consequently, the overall process requires great technical effort and is moreover uneconomic. Another process (EP-A-0,355,774) uses 2,4-dichloro-5-fluorobenzoic acid esters as starting materials. Although a halex reaction (chlorine/fluorine exchange) of the 2,4-dichloro-5-fluorobenzoic acid esters makes it possible to exchange the 4-chloro atom for fluorine with relatively high selectivity, isomers are always formed in an amount of 3 to 8%. However, these isomers can only be separated off with very great technical effort. Moreover, the yields are only low when simple esters are used, since these esters only have a low stability under the reaction conditions. Satisfactory to good yields are not achieved unless bulky esters or esters of higher alcohols are used. However, the steric hindrance impedes the hydrolysis of these esters to the benzoic acid.

The processes known hitherto for the preparation of 2,3-dichloro-4,5-difluorobenzoic acid prove even less favorable. This compound is known from EP-A-0,230,947 and EP-A-0,159,388. It can be prepared by denitrating chlorination or via a multistep synthesis starting from benzonitriles and passing via brominated compounds. The technical effort associated with such a multistep synthesis is very great and leads to high manufacturing costs. Furthermore, the overall yields are rather low due to the multistep process.

The process described in EP-A-0,230,947 requires the use of both highly toxic cyanide and elemental bromine to prepare the brominated compounds. One of the most important requirements made of modern drugs is that they must not contain even traces of bromine. Consequently, both the precursors and the intermediates have to be prepared as far as possible by bromine-free methods.

The process described in EP-A-0,159,388 starts from nitro compounds, which are converted to the desired products by exchange of the nitro group by means of chlorine at high temperatures. The disadvantages of this process are that the requisite starting materials are already difficult to prepare and also that the reactions do not proceed satisfactorily in accordance with the reaction equilibria because the desired products have high boiling points and therefore cannot be distilled out of the reaction mixture in the way which is generally required for a smooth reaction course, so this synthesis route cannot be carried out industrially with Justifiable economic effort.

There was therefore a very great need for a new process for the preparation of 4,5-difluorobenzoic acids, -benzoic acid derivatives and -benzaldehydes chlorinated in the 2-position and optionally in the 3-position which does not exhibit the described disadvantages and which provides the desired compounds not only with relatively little technical effort, but also in high yield and high purity.

This object is achieved by a process for the preparation of compounds of the formula

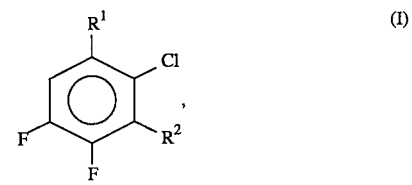

in which $R^1$ is —CN, —COOH, —COOR', R' being an organic radical having 1 to 6 carbon atoms, —CONH$_2$, —COCl or —CHO and $R^2$ is H or Cl. It comprises reacting a compound of the formula

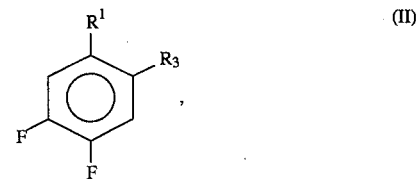

in which $R^1$ is as defined above and $R^3$ is H or Cl, with a chlorinating agent in the presence of a chlorination catalyst at −10° to 200° C.

One advantage is that the process according to the invention is not restricted to a small number of starting materials, but can be applied to a large number of different compounds. Thus, starting materials which are generally suitable are compounds of the formula (II) in which $R^1$ is —CN, —COOH, —COOR', R' being an organic radical having 1 to 6 carbon atoms, for example a methyl, ethyl, propyl, isopropyl, butyl, isobutyl, pentyl or hexyl group, —CONH$_2$, —COCl or —CHO, especially —CN, —COOH, —COOR' or —COCl, preferably —CN, —COOH or —COCl and particularly preferably —CN or —COOH, and $R^3$ is H or Cl.

It is also possible to use mixtures of compounds of the formula (II) in any desired combination. These include on the one hand mixtures containing compounds where $R^3$=H and $R^3$=Cl, and on the other hand mixtures in which the compounds have different radicals $R^1$, as well as combinations of these two mixture variants.

The abovementioned starting materials are largely derived from 3,4-difluorobenzoic acid (equivalent to 4,5-difluorobenzoic acid) and can be prepared therefrom. One way of preparing 3,4-difluorobenzoic acid (EP-A-0,431,294) is to decarboxylate 4,5-difluorophthalic acid, which in turn can be obtained from 4,5-dichlorophthalic anhydride by chlorine/fluorine exchange (halex reaction) and subsequent hydrolysis of the 4,5-difluorophthalic anhydride (EP-A-0, 055,630). An alternative possibility is to introduce the two fluorine atoms into 3,4-dichloro compounds by means of a halex reaction (N. Yazawa et al., Chem. Letto (1989), 2212 to 2216), 3,4-dichlorobenzonitrile, 3,4-dichlorobenzoyl chloride or 3,4-dichlorobenzaldehyde being particularly suitable.

The corresponding 3,4-difluoro compounds can then be converted to the corresponding acid by methods known in principle in the literature, such as acid or alkaline hydrolysis.

In the process according to the invention, the 3,4-difluoro compound (equivalent to 4,5-difluoro compound) used as the starting material is first converted to a 2-chloro-4,5-difluoro compound by chlorination and then converted to the corresponding 2,3-dichloro-4,5-difluoro compound by the introduction of a further chlorine atom. Depending on which product is to be prepared, the reaction can be continued either only as far as the 2-chloro-4,5-difluoro compound, which can optionally be converted to 2-chloro-4,5-difluorobenzoic acid, or else as far as the 2,3-dichloro-4,5-difluoro compound, which can optionally be processed to 2,3-dichloro-4,5-difluorobenzoic acid.

The present invention also opens up the possibility of preparing both the 2-chloro-4,5-difluoro compounds and the 2,3-dichloro-4,5-difluoro compounds. The invention further makes it possible, through the choice of process conditions, specifically to influence the formation of both products and voluntarily to control, within relatively wide limits, the ratio in which the two products are formed. Mixtures of any desired composition can thus be specifically prepared right from the outset.

One variant of the process according to the invention comprises reacting the compound of the formula (II) in which $R^3$ is H with the chlorinating agent to give the corresponding compound substituted by chlorine in the 2-position, and then reacting this compound with a chlorinating agent, optionally after isolation of the intermediate but especially without isolation of the intermediate, to give the corresponding compound dichlorinated in the 2,3-position.

It is also possible, however, to react 2-chloro-4,5-difluoro compounds (of the formula (II) in which $R^3$ is Cl), not prepared by chlorination of the corresponding 3,4-difluoro compound (or 4,5-difluoro compound), with a chlorinating agent to give the corresponding compound dichlorinated in the 2,3-position.

It is surprising that when the 3,4-difluoro compounds are chlorinated, a chlorine atom initially enters the 2-position with high selectivity even though the directing effects of the substituents present on the benzene ring would normally be expected to induce very selective substitution in the 3-position (J. March, Adv. Org. Chem. (1985, 3rd edition), 16 to 18, 453 to 460). Also surprising is the fact that in the second substitution step, a further chlorine atom enters the 3-position, again with high selectivity. Here, in addition to the meta-directing effect of the carboxyl group, there is also a possible contribution from the ortho-directing effect exerted by the chlorine atom introduced into the 2-position. Thus the corresponding 2,3-dichloro-4,5-difluoro compound, especially 2,3-dichloro-4,5-difluorobenzoic acid, is unexpectedly produced without the formation of significant amounts of a trichlorinated compound or other isomers as a result of further chlorination, even at high conversions.

The reaction is carried out in the presence of a chlorination catalyst. Suitable chlorination catalysts are iodine, iodine trichloride, iodine pentachloride, iron, iron (II) chloride, iron (III) chloride, aluminum chloride, disulfur dichloride, antimony trichloride and/or antimony pentachloride, especially iodine, iodine trichloride, iron(II) chloride and/or disulfur dichloride and preferably iodine and/or disulfur dichloride. It is also possible, however, to use mixtures of the abovementioned chlorination catalysts in any desired combination.

The chlorination catalyst is used in catalytic amounts, i.e. not in a stoichiometric amount, based on the compound to be converted. It is conventional to use 0.001 to 0.05 mol, especially 0.002 to 0.02 tool, of chlorination catalyst per mole of compound to be chlorinated.

The reaction is carried out using a chlorinating agent, suitable chlorinating agents being chlorine and/or a chlorine-releasing agent. A particularly suitable chlorinating agent is chlorine.

Chlorine-releasing agents which can be used are phosphorus trichloride, phosphorus pentachloride, antimony pentachloride, iodine trichloride, sulfur dichloride, disulfur dichloride and manganese tetrachloride, especially phosphorus pentachloride and iodine trichloride and preferably phosphorus pentachloride.

When carrying out the reaction, it has proved useful in many cases to work with less than the stoichiometrically required amount of chlorine or chlorine-releasing agents. It is convenient to use 0.05 to 0.95, especially 0.1 to 0.9 and preferably 0.25 to 0.85 mol of chlorine or chlorine-releasing agent per equivalent of hydrogen atom to be substituted. To prepare 2-chloro-4,5-difluoro compounds from 3,4-difluoro compounds, it is normal practice to use 0.1 to 0.8 mol, preferably 0.25 to 0.6 mol, of chlorine or chlorine-releasing agent per mole of 3,4-difluoro compound. To convert 2-chloro-4,5-difluoro compounds to the corresponding 2,3-dichloro-4,5-difluoro compounds, 0.3 to 0.95 mol, preferably 0.5 to 0.85 mol, of chlorine or chlorine-releasing agent is generally added per mole of 2-chloro-4,5-difluoro compound. If the 2,3-dichloro-4,5-difluoro compounds are prepared from the 3,4-difluoro compounds, 0.3 to 1.5 mol, preferably 0.7 to 1.2 mol, of chlorine or chlorine-releasing agent are reacted per mole of 3,4-difluoro compound. The amount of chlorine which is actually required (or the so-called chlorine yield) is also appreciably dependent on the gas feed, the intimate mixing of the reactants and the type and shape of the reaction apparatuses used.

It has proved convenient to select the chlorine flow rates or, when using chlorine-releasing agents, the chlorine release rates to be about 5 to about 600, especially about 20 to about 400 and preferably about 40 to about 200, ml per hour, based in each case on 1 g of the compound to be chlorinated.

The operating temperatures are from $-10°$ to $200°$ C. In one particular embodiment, the reaction is carried out in the presence of a solvent at temperatures from $-10$ to $80$, especially $0$ to $70$ and preferably $10$ to $50$, °C. Suitable solvents are chlorosulfonic acid, sulfuric acid or oleum, especially chlorosulfonic acid or oleum and preferably chlorosulfonic acid.

Mixtures of the abovementioned solvents can also be successfully used, especially mixtures containing at least 10% by weight of chlorosulfonic acid and especially 10 to 90% by weight of chlorosulfonic acid.

In another embodiment of the process, the reaction is carried out in the absence of a solvent at 100 to 200 and especially $130°$ to $180°$ C.

It can be useful in a number of cases to add a fluoride-trapping agent to the bottom of the chlorination column, and especially to the water generally added in order to precipitate the product dissolved in the solvents used, in order to prevent the hydrogen fluoride corrosion which can occur extensively in such reactions, suitable fluoride-trapping agents being calcium salts such as calcium chloride, calcium sulfate and calcium hydroxide, and silicic acid, silica gels and silicon dioxide. It is also possible to use mixtures of the abovementioned fluoride-trapping agents.

The desired useful products of the formula (I) (these include especially 2,3-dichloro-4,5-difluorobenzoic acid and 2-chloro-4,5-difluorobenzoic acid and functional derivatives thereof) can be isolated for example by dilution of the reaction mixture with water and subsequent filtration. Their further purification is conveniently effected by recrystallization, optionally with the addition of activated charcoal. They can also be purified by column chromatography. A particularly easy method of purification is to convert the carboxylic acid or carboxylic acid derivatives to the corresponding carboxylic acid chlorides and separate the latter by fractional distillation. A further advantage of this method is that the acid chlorides can then be further processed directly to the corresponding useful products. The acid chlorides can be prepared by the conventional methods from the carboxylic acids contained in the crude mixture.

The yields of 2,3-dichloro-4,5-difluorobenzoic acid and 2-chloro-4,5-difluorobenzoic acid are normally 60 to 90%. Small amounts of 2,3,6-trichloro-4,5-difluorobenzoic acid are formed as a by-product; this can be separated off by the described methods and optionally used for other syntheses.

The functional derivatives of 2,3-dichloro-4,5-difluorobenzoic acid and/or of 2-chloro-4,5-difluorobenzoic acid which are optionally prepared according to the invention can optionally be converted to the acids by the methods known in principle in the literature (acid or basic hydrolysis), as indicated for the 3,4-difluoro compounds. All the process steps can be carried out under atmospheric pressure, reduced pressure or excess pressure. The following Examples illustrate the process without implying a limitation.

EXAMPLE 1

470 g (2.44 mol) of 2-chloro-4,5-difluorobenzoic acid and 14 g (55 mmol) of iodine are initially placed in 1900 g of chlorosulfonic acid. Chlorine is introduced at 30° C. for 6.5 h (11 to 12 l/h). The initially dark green mixture changes color to brown during the slightly exothermic reaction. It is then added dropwise to 3000 g of ice, with brine cooling, and the yellowish product which has precipitated out is filtered off with suction and washed twice with 500 g of water to give 620 g of a moist product, which is dried at 45° C. under vacuum (585 g dry weight). 357 g (3 mol) of thionyl chloride are added to the dry melted-on product over 3 h at 70° C. and the mixture is kept for 6 h at 80° C. The excess thionyl chloride (80 g) is then stripped off under a weak vacuum (100 mbar). The residual, clear, light yellowish solution is subjected to fractional distillation under vacuum to give:

99.7 g (0.47 mol, 19%) of 2-chloro-4,5-difluorobenzoyl chloride (b.p. 9 Torr/95° C.) 381.5 g (1.55 mol, 64%) of 2,3-dichloro-4,5-difluorobenzoyl chloride (b.p. 8 to 9 Torr/106° to 109° C.) 51.6 g (0.185 mol, 8%) of 2,3,6-trichloro-4,5-difluorobenzoyl chloride (b.p. 9 Torr/122° to 124° C.)

The aqueous mother liquor is extracted with methyl tertbutyl ether (MTBE). After drying of the organic phase and removal of the solvent, 32.0 g of a yellow solid are obtained which contains 26.7 g (0.14 mol, 6%) of 2-chloro-4,5-difluorobenzoic acid according to gas chromatographic (GC) analysis. 2,3-Dichloro-4,5-difluorobenzoic acid: $^{19}F$ NMR [DMSO-$d_6$, ppm, CFCl$_3$]:

$\delta = -127.72$ (dd, 1F, $J_{AB} = 8.1$ Hz, $J_{BC} = 22.8$ Hz, Ar—$F^4$ (B))
$-134.76$ (dd, 1F, $J_{AC} = 10.2$ Hz, $J_{BC} = 22.2$ Hz, ArF$^5$ (C))

EXAMPLE 2

100 g (0.52 mol) of 2-chloro-4,5-difluorobenzoic acid and 1 g of iodine are initially placed in 500 g of oleum. Chlorine is introduced at 35° to 50° C. for 2.5 h (8 to 10 l/h). When chlorination has ended, the mixture is poured onto 400 g of ice and the solid which has precipitated out is filtered off to give 286 g of a moist product, which is reacted with thionyl chloride (2 mol) at 80° C. to give a mixture of acid chlorides. These are separated by fractional distillation, as described in Example 1, to give 7 g (33 mmol, 6%) of 2-chloro-4,5-difluorobenzoyl chloride, 76 g (0.31 mol, 60%) of 2,3-dichloro-4,5-difluorobenzoyl chloride and 29.8 g (0.11 mol, 20%) of 2,3,6-trichloro-4,5-difluorobenzoyl chloride. The boiling points are as described in Example 1. The main fraction is purified by hydrolysis with water and recrystallization of the resulting 2,3-dichloro-4,5-difluorobenzoic acid from hot water to give colorless crystals (68.5 g) melting at 130.5° C. (TLC).

EXAMPLE 3

1.5 g of iron(III) chloride and 31.5 g (0.2 mol) of 3,4-difluorobenzoic acid are initially placed in 200 g of oleum at 25° to 35° C. 7 /h of chlorine are introduced over 4 h and the mixture is diluted with 100 g of water, with intensive cooling, to give 33 g of a moist mixture of benzoic acids, the mother liquor being discarded. Said mixture is reacted with thionyl chloride at 80° C. and the volatile constituents (37 g) are distilled off. According to gas chromatographic analysis, the mixture is composed of 11.2 g (64 mmol, 32%) of 3,4-difluorobenzoyl chloride, 14.7 g (70 mmol, 35%) of 2-chloro-4,5-difluorobenzoyl chloride and 10.9 g (44 mmol, 22%) of 2,3-dichloro-4,5-difluorobenzoyl chloride. The mixture, together with the crude mixtures of several analogous batches, is purified by fractionation as described in Example 1. The 3,4-difluorobenzoyl chloride passes over at 9 Torr/79° to 80°.

EXAMPLE 4

0.5 g of disulfur dichloride is initially placed in 100 g of oleum/100% sulfuric acid (1:1), and 10.9 g (69 mmol) of 3,4-difluorobenzoic acid are added. The mixture is chlorinated between −5° and 0° C. (6 h) and then diluted with 100 g of ice. The moist product is filtered off (15.2 g) to give 13.8 g of crude product after drying. This is converted to the acid chlorides by the method described in Example 1 and these acid chlorides, together with other batches, were separated by fractionation. 3.3 g (19 mmol, 27%) of 3,4-difluorobenzoyl chloride, 7.2 g (34 mmol, 50%) of 2-chloro-4,5-difluorobenzoyl chloride and 2.6 g (11 mmol, 15%) of 2,3-dichloro-4,5-difluorobenzoyl chloride are found in the mixture by quantitative GC analysis.

EXAMPLE 5

15.8 g (0.1 mol) of 3,4-difluorobenzoic acid are chlorinated (1 l/h) in 50 g of chlorosulfonic acid and 50 g of 100% sulfuric acid in the presence of 0.5 g of iron chloride at 40° C. for 2 h. After this time, the chlorine is purged and 50 g of ice are added. The mixture of carboxylic acids is filtered off (16.0 g dry weight) and the products are separated by fractional crystallization from water or hexane, any products remaining in the water due to residual solubility being recycled by extraction with MTBE. 2.3 g (14.5 mmol, 15%) of 3,4-difluorobenzoic acid starting material, 8.1 g (42 mmol, 42%) of 2-chloro-4,5-difluorobenzoic acid and 4.3 g (19 mmol, 19%) of 2,3-dichloro-4,5-difluorobenzoic acid, each with purities of >95%, are obtained as colorless to light yellowish solids.

EXAMPLE 6

3 g of iodine and 2 g of disulfur dichloride are initially placed in 1000 g of chlorosulfonic acid. 139.1 g (1 mol) of 3,4-difluorobenzonitrile are added at 0° C. The introduction of chlorine is started (10 l/h) and the temperature is raised to 30° C. over 30 min. After 2.5 h the chlorine supply is stopped and excess dissolved chlorine is purged. 500 g of water are added dropwise, with intense cooling, and the whole mixture is heated for 2 h at 140° C. (hydrolysis of the benzamides formed as intermediates, and of the nitriles). After this time, cooling is continued and the mixture is diluted with a further 800 g of water. The solid which precipitates out is filtered off with suction (245 g moist weight, 190 g dry weight) and reacted with thionyl chloride (2 mol) at 80° C. The acid chlorides are separated by fractionation to give the following colorless liquids:

33.3 g (0.19 mol, 19%) of 3,4-difluorobenzoyl chloride (b.p. 9 Torr/79° C.)

97.8 g (0.46 mol, 46%) of 2-chloro-4,5-difluorobenzoyl chloride (b.p. 9 Torr/95° C.)

71.2 g (0.29 mol, 29%) of 2,3-dichloro-4,5-difluorobenzoyl chloride (b.p. 8 to 9 Torr/107° to 108° C.)

2.9 g (10 mmol, 1%) of 2,3,6-trichloro-4,5-difluorobenzoyl chloride (b.p. 9 Torr/122° to 124° C.)

If the 139.1 g (1 mol) of 3,4-difluorobenzonitrile are replaced with 157.1 g (1 mol) of 3,4-difluorobenzamide, the procedure otherwise being as indicated, essentially the same result is obtained.

EXAMPLE 7

211 g (1 mol) of 2-chloro-4,5-difluorobenzoyl chloride are introduced into 500 g of chlorosulfonic acid, and 3 g of iodine are added. The mixture is chlorinated (10 l/h) for 1.7 h at 40° C. and then diluted with water (500 g), with stirring, the temperature being allowed to rise to 80° C. In this procedure, the acid chlorides initially present in the solvent are hydrolyzed in 2 h to the carboxylic acids, which are isolated by filtration after cooling to 0° C. After drying, the mixture is reacted with thionyl chloride (2 mol) at 80° C. and excess thionyl chloride is then distilled off. The mixture is then distilled, as indicated in Example 1, to give 46.4 g (0.22 mol, 22%) of 2-chloro-4,5-difluorobenzoyl chloride and 174.9 g (0.71 mol, 71%) of 2,3-dichloro-4,5-difluorobenzoyl chloride.

We claim:

1. A process for the preparation of a compound of the formula I

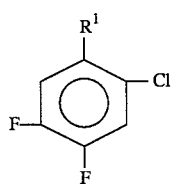

in which $R^1$ is —COOH, —COCl, —CN, or —CONH$_2$, which comprises chlorinating a compound of the formula II

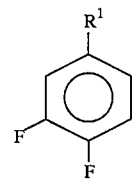

with chlorine in a reaction medium comprising a solvent and an iodine-containing, a disulfur dichloride-containing, or iron chloride-containing chlorination catalyst, or a combination of said chlorination catalysts, in the temperature range of $-10°$ to $200°$, wherein the $R^1$ of formula I at the completion of said chlorinating step is identical to the $R^1$ of formula II.

2. The process as claimed in claim 1, wherein $R^1$ of the compound of formula II is —COOH; the resulting compound of formula I is reacted with thionyl chloride; and the compound 2-chloro-4,5-difluorobenzoyl chloride is recovered as the product of the process.

3. The process as claimed in claim 1, wherein $R^1$ of the compound of formula II is —CONH$_2$ or —CN; the resulting compound of formula I is hydrolyzed; the resulting hydrolysis product is reacted with thionyl chloride; and the compound 2-chloro-4,5-difluorobenzoyl chloride is recovered as the product of the process.

4. The process as claimed in claim 1, wherein the compound of formula I undergoes further chlorinating with chlorine in a said reaction medium, in said temperature range, to obtain the compound Ia

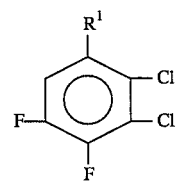

in which $R^1$ is identical to the $R^1$ of the compound of formula II.

5. The process as claimed in claim 1, wherein said solvent is sulfuric acid, oleum, chlorosulfonic acid, or a mixture thereof.

6. The process as claimed in claim 1, wherein said reaction medium contains 0.001 to 0.05 mol of chlorination catalyst per mole of compound of formula II.

7. The process as claimed in claim 1, wherein the amount of chlorine is 0.05 to 0.95 mol per equivalent of H to be substituted on said compound of formula II.

8. The process as claimed in claim 1, wherein said temperature range is from 10° to 50°.

9. A process for the preparation of a compound of the formula I

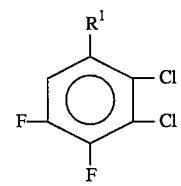

in which $R^1$ is —COOH, —COCl, —CN, or —CONH$_2$, which comprises chlorinating a compound of the formula II

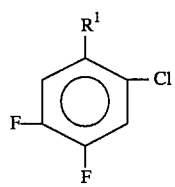

with chlorine in a reaction medium comprising a solvent and an iodine-containing, a disulfur dichloride-containing, or iron chloride-containing chlorination catalyst, or a combination of said chlorination catalysts, in the temperature range of −10° to 200°, wherein the $R^1$ of formula Ia at the completion of said chlorinating step is identical to the $R^1$ of formula IIa.

10. The process as claimed in claim 9, wherein $R^1$ of the compound of formula IIa is —COOH; the resulting compound of formula Ia is reacted with thionyl chloride; and the compound 2,3-dichloro-4,5-difluorobenzoyl chloride is recovered as the product of the process.

11. The process as claimed in claim 9, wherein said solvent is sulfuric acid, oleum, chlorosulfonic acid, or a mixture thereof.

12. The process as claimed in claim 9, wherein said reaction medium contains 0.001 to 0.05 mol of chlorination catalyst per mole of compound of formula II.

13. The process as claimed in claim 9, wherein the amount of chlorine is 0.05 to 0.95 mol per equivalent of H to be substituted on said compound of formula II.

14. The process as claimed in claim 9, wherein said temperature range is from 10° to 50°.

15. The process as claimed in claim 9, wherein $R^1$ is —COOH or —COCl.

* * * * *